US008703693B2

(12) United States Patent
Wang

(10) Patent No.: US 8,703,693 B2
(45) Date of Patent: Apr. 22, 2014

(54) ADRENOMEDULLIN AND ADRENOMEDULLIN BINDING PROTEIN FOR ISCHEMIA/REPERFUSION TREATMENT

(75) Inventor: Ping Wang, Rosyln, NY (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 768 days.

(21) Appl. No.: 11/547,072

(22) PCT Filed: Mar. 30, 2005

(86) PCT No.: PCT/US2005/010822
§ 371 (c)(1),
(2), (4) Date: Jun. 29, 2007

(87) PCT Pub. No.: WO2005/097172
PCT Pub. Date: Oct. 20, 2005

(65) Prior Publication Data
US 2008/0051316 A1   Feb. 28, 2008

Related U.S. Application Data

(60) Provisional application No. 60/557,935, filed on Mar. 31, 2004.

(51) Int. Cl.
| | |
|---|---|
| *A61K 38/00* | (2006.01) |
| *A61P 39/06* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 17/00* | (2006.01) |
| *C07K 1/00* | (2006.01) |

(52) U.S. Cl.
USPC ............ 514/1.1; 514/15.1; 530/300; 530/350

(58) Field of Classification Search
None
See application file for complete search history.

(56) References Cited

U.S. PATENT DOCUMENTS

| | | | |
|---|---|---|---|
| 5,639,855 A | 6/1997 | Kitamura et al. | |
| 5,851,528 A * | 12/1998 | Ko et al. | 424/185.1 |
| 6,620,615 B1 | 9/2003 | Gould-Rothberg | |
| 6,864,237 B2 * | 3/2005 | Wang | 514/2.4 |
| 6,884,781 B2 * | 4/2005 | Wang | 424/85.2 |
| 8,324,151 B2 | 12/2012 | Wang | |
| 2003/0216291 A1 | 11/2003 | Wang | |
| 2005/0181983 A1 * | 8/2005 | Wang | 514/2 |
| 2006/0178308 A1 * | 8/2006 | Schwaeble et al. | 514/12 |
| 2007/0025915 A1 * | 2/2007 | Cuttitta et al. | 424/1.49 |
| 2008/0051315 A1 * | 2/2008 | Kandel et al. | 514/1 |
| 2008/0051316 A1 * | 2/2008 | Wang | 514/2 |
| 2009/0202518 A1 | 8/2009 | Wang | |
| 2009/0297498 A1 | 12/2009 | Wang | |
| 2011/0105399 A1 | 5/2011 | Wang | |
| 2013/0096048 A1 | 4/2013 | Wang | |

FOREIGN PATENT DOCUMENTS

WO     2005097172 A2     10/2005

OTHER PUBLICATIONS

Elsasser et al. Adrenomedullin binding protein in the plasma of multiple species: characterization by radioligand blotting. Endocrinology. Oct. 1999; 140(10):4908-11.*

Elsasser et al. Adrenomedullin binding protein in the plasma of multiple species: characterization by radioligand blotting. Endocrinology. Oct. 1999;140(10):4908-11.*

Claims of Japanese Application No. 2007-506527 as pending on issue of last-issued Office Action; Last-issued Office Action in Japanese Application No. 2007-506527 as issued on Jan. 7, 2012; Claims as finally allowed in Japanese Application No. 2007-506527.*

Claims of European Application No. 1 742 651 as pending on issue of last-issued Office Action; Last-issued Office Action in European Application No. 1 742 651 as issued on Sep. 2, 2009; Claims as finally allowed in European Application No. 1 742 651.*

Claims of Canadian Application No. 2,562,957 as pending on issue of last-issued Office Action; Last-issued Office Action in Canadian Application No. 2,562,957 as issued on Nov. 7, 2012; Claims as finally allowed in Canadian Application No. 2,562,957.*

Claims of Australian Application No. 2005231395 as pending on issue of last-issued Office Action; Last-issued Office Action in Australian Application No. 2005231395 as issued on Nov. 9, 2010; Claims as finally allowed in Australian Application No. 2005231395.*

Elsasser T.H. et al., "Adrenomedullin Binding Protein in the Plasma of Multiple Species: Characterization by Radioligand Blotting"; Endocrinology, 1999, vol. 140, No. 10, pp. 4908-4911.

Kato K. et al., "Adrenomedullin gene delivery attenuates myocardial infarction and apoptosis after ischemia and reperfusion"; Am. J. Physiol. Heart Circ. Physiol., 2003, vol. 285, pp. H1506-H1514.

Tsuruda T. and Burnett, Jr. J.C., "Adrenomedullin—An Autocrine/Paracrine Factor for Cardiorenal Protection"; Circulation Research, 2002, pp. 625-627.

(Continued)

*Primary Examiner* — Maury Audet
(74) *Attorney, Agent, or Firm* — Amster, Rothstein & Ebenstein LLP

(57) ABSTRACT

Methods of treating a mammal at risk for ischemia-reperfusion injury are provided. The methods comprise administering an adrenomedullin binding protein-1 (AMBP-1) to the mammal in sufficient amount to reduce the injury. Also provided are methods of treating a mammal at risk for ischemia-reperfusion injury to the bowel. The methods comprise administering adrenomedullin to the mammal in sufficient amount to reduce the injury.

7 Claims, No Drawings

(56) References Cited

OTHER PUBLICATIONS

The Supplementary European Search Report for European Application No. EP 05732325.5, May 2009.
Beltowski et al. "Adrenomedullin—what do we know 10 years since its discovery?" Pol. J. Pharmacol., 56 (2004), pp. 5-27.
Yin et al. "Adrenomedullin protects against myocardial apoptosis after ischemia/reperfusion through activation of Akt-GSK signaling." Hypertension (Baltimore) 43:1, 109-116, 2009.
Lien, et al. "Pathogenesis of renal ischemia/reperfusion injury: lessons from knockout mice." Life Sciences, 74:5 (2003), pp. 543-552.
Fowler et al. "Adrenomedullin and adrenomedullin binding protein-1: their role in the septic response." J. Surgical Res., 109:2 (2003), pp. 175-181.
Carrizo et al. "Adrenomedullin and adrenomedullin-binding protein-1 downregulate inflammatory cytokines and attenuate tissue injury after gut ischemia-reperfusion." Surgery, 141:2 (2007) pp. 245-253.
Notice of Allowance received by the Canadian Intellectual Property Office dated Jan. 11, 2013 in connection with Canadian Patent Application No. 2,562,957, 1 page.
Shah K G et al., entitled "Attenuation of renal ischemia and reperfusion injury by human adrenomedullin and its binding protein," J Surg Res. Sep. 2010; 163(1):110-117.
Dwivedi A J et al., entitled "Adrenomedullin and Adrenomedullin Binding Protein-1 Prevent Acute Lung Injury after Gut Ischemia-Reperfusion," J Am Coll Surg 2007;205:284-293.
Carrizo G J et al., enititled "Adrenomedullin and adrenomedullin-binding protein-1 downregulate inflammatory cytokines and attenuate tissue injury after guy ischemia-reperfusion," Surgery 2007;141:245-53.
Zhang F et al., entitled "Human adrenomedullin combined with human adrenomedullin binding protein-1 is protective in gut ischemia and reperfusion injury in the rat," Regul Pept. Jan. 8, 2009; 152(1-3): 82-87.
Yang J et al., entitled "Human Adrenomedullin and Its Binding Protein Attenuate Organ Injury and Reduce Mortality After Hepatic Ischemia-Reperfusion," Ann Surg. Feb. 2009; 249(2): 310-317.
Higuchi S et al., entitled "Gut Hyperpermiability after Ischemia and Reperfusion Attenuation with Adrenomedullin and its Binding Protein Treatment," Int J Clin Exp Pathol (2008) 1, 409-418.
Chaung W W et al., entitled "Peripheral Administration of Human Adrenomedullin and its Binding Protein Attenuates Stroke-Induced Apoptosis and Brain Injury in Rats," Mol Med 17(9-10) 1075-1083, Sep.-Oct. 2011.
Australian Notice of Acceptance dated Jun. 6, 2011 corresponding to Australian Patent Application No. 2005231395.
Australian Examiner's report No. 2 dated Nov. 9, 2010 corresponding to Australian Patent Application No. 20055231395.
Australian Examiner's First Report dated Nov. 6, 2009 corresponding to Australian Patent Application No. 2005231395.
European Decision to Grant Patent dated Feb. 10, 2011 corresponding to European Patent Application No. 05 732 325.5.
Canadian Office Action dated Nov. 1, 2011 corresponding to Canadian Application No. 2,562,957.
Preliminary Notice of Reasons for Rejection dated Jan. 7, 2011 corresponding to Japanese Patent Application No. 2007-506527.

\* cited by examiner

ADRENOMEDULLIN AND ADRENOMEDULLIN BINDING PROTEIN FOR ISCHEMIA/REPERFUSION TREATMENT

CROSS-REFERENCE TO RELATED APPLICATION

This is a U.S. National Phase of PCT Application No. PCT/US2005/010822, filed Mar. 30, 2005, which claims the benefit of U.S. Provisional Application No. 60/557,935, filed Mar. 31, 2004.

BACKGROUND OF THE INVENTION (1) Field of the Invention

The present invention generally relates to treatments for preventing or minimizing ischemia-reperfusion injury. More specifically, the invention is directed to the administration of administration of adrenomedullin binding protein-1 to mammals at risk for ischemia-reperfusion injury.

(2) Description of the Related Art

Tissue ischemia leads to several chemical events occur that can result in cellular dysfunction and necrosis, due to lack of oxygen in the tissues as well as induction of proinflammatory cytokines, particularly tumor necrosis factor-α (TNF-α), and the interleukins IL-1β, IL-6 and IL-10. When blood flow is restored (reperfusion), another series of events occur that produces additional injury, caused to a great extent by free radical formation, believed to be produced in part by neutrophils that are activated at the reperfusion site. In many instances, the reperfusion injury is more severe than the ischemic injury, especially if the ischemia occurs for only a short period of time.

Ischemia-reperfusion injury can occur at any time blood flow is interrupted and then restored. Examples include myocardial injury following balloon angioplasty or tPA treatment; decompression fasciotomy for severe compartment syndrome following a crush injury; restoration of blood flow following a stroke; restoration of blood flow into a transplanted organ, particularly a kidney or liver; bowel disorders such as irritable bowel syndrome or Chrohn's disease; and neuropathy due to vascular dysfunction in a diabetic.

Ischemia-reperfusion injury is often treated with pentoxifilline, a methyl xanthine derivative that inhibits neutrophil activation, and/or allopurinol, a xanthine oxidase inhibitor that reduces toxic oxygen radicals. Other treatments include antibodies to neutrophil chemoattractants. However, these treatments are often ineffective or only partially effective. There is thus a need for new treatments for ischemia-reperfusion injury.

Adrenomedullin (AM), a newly reported and potent vasodilatory peptide, is an important mediator involved in both physiological and pathological states. Human AM, a 52-amino acid peptide, was first isolated and reported in 1993. AM has a carboxy terminal amidated residue and a 6-member ring structure formed by an intramolecular disulfide bond near the amino terminus, and is available commercially. Rat adrenomedullin has 50 amino acids with 2 amino acid deletions and 6 substitutions as compared to human adrenomedullin. Adrenomedullin transcripts and protein are expressed in a large number of tissues, and circulating levels of adrenomedullin were observed under normal as well as pathophysiological conditions.

In 1999, Elsasser et al. (Endocrinol. 140:4908-11) reported that specific adrenomedullin binding proteins (AMBP) exist in the plasma of several species including humans. More recently, the binding protein AMBP-1 has been identified in human plasma and has been shown to be identical to human complement factor H. AMBP-1 enhances adrenomedullin-mediated induction of cAMP in fibroblasts, augments the adrenomedullin-mediated growth of a cancer cell line, and suppresses the bactericidal capability of adrenomedullin on *E. coli*.

Other studies have also shown that AM and AMBP-1 have anti-inflammatory properties in a sepsis model. That work found that adrenomedullin binding protein-1 (AMBP-1) is limiting relative to adrenomedullin during shock, which limits the effectiveness of adrenomedullin therapy for reducing deleterious effects of shock. Administration of AMBP-1 alleviates this adrenomedullin hyporesponsiveness and is thus a useful therapy for shock, either alone or with AM treatment. See U.S. patent application Ser. No. 10/729,193, filed Dec. 5, 2003.

Additionally, AM has been found to be effective in treating ischemia-reperfusion injury caused by myocardial infarction (Kato et al., Am. J. Physiol. Heart Circ. Physiol. 285:H1506-14, 2003), as well as ischemic renal injury (Nishimatsu et al., Circulation Res. 90:625-7, 2002). There is thus a need to determine whether AM treatment is effective for reducing or preventing other ischemic/reperfusion injury, and whether AM and AMBP-1 treatments are effective with ischemia/reperfusion injury. The present invention addresses that need.

SUMMARY OF THE INVENTION

Accordingly, the present invention is based on the discovery that treatment with AM+AMBP-1 is effective in reducing or eliminating ischemia-reperfusion injury resulting from ischemic bowel. See Examples. With this discovery, the skilled artisan would understand that AMBP-1 treatment, with or without AM, is effective with any ischemia/reperfusion injury and that AM treatment alone is effective in treatment of ischemic bowel.

Thus, in some embodiments, the invention is directed to methods of treating a mammal at risk for ischemia-reperfusion injury. The methods comprise administering an adrenomedullin binding protein-1 (AMBP-1) to the mammal in sufficient amount to reduce the injury.

In other embodiments, the invention is directed to methods of treating a mammal at risk for ischemia-reperfusion injury to the bowel. The methods comprise administering adrenomedullin to the mammal in sufficient amount to reduce the injury.

DETAILED DESCRIPTION OF THE INVENTION

As established in the Examples, treatment of ischemic bowel with AM+AMBP-1 reduces or eliminates ischemia-reperfusion injury. Since insufficient endogenous AMBP-1 was found to limit the effectiveness of AM for treatment of shock (see U.S. patent application Ser. No. 10/729,193, filed Dec. 5, 2003), it would be understood that such is also the case for the use of AM alone for the treatment of ischemia-reperfusion injury. The skilled artisan would thus expect AMBP-1 treatment alone to be effective in the treatment of ischemia-reperfusion injury, because the added AMBP-1 would then be available to bind with the excess AM present to be effective in reducing or eliminating ischemia-reperfusion injury. Without being bound to any particular mechanism, it is believed that the binding of AM with AMBP-1 causes a reduction of inflammation and increases vascular hyporesponsiveness by preventing increases in inflammatory cytokines, particularly IL-1β, IL-6, IL-10 and TNF-α, which are otherwise induced by the ischemia and/or reperfusion. It would also be expected that AM in combination with AMBP-1 would be more effective than AMBP-1 treatment alone, particularly if the AMBP-1 treatment then makes AM limiting.

Thus in some embodiments, the invention is directed to methods of treating a mammal at risk for ischemia-reperfusion injury. The methods comprise administering an adrenomedullin binding protein-1 (AMBP-1) to the mammal in sufficient amount to reduce the injury.

AMBP-1 is preferably administered along with adrenomedullin, in order to maximize the therapeutic effect of the AMBP-1 administration.

These methods can be effectively used in any mammalian species, including experimental animals such as rat, mouse and guinea pig; domesticated animals such as horse, dog, pig, rabbit, cat and ferret; as well as humans.

The AMBP-1 and adrenomedullin administered in these methods can be from any mammalian species, but is preferably from the same mammalian species being treated, to minimize the possibility of allergic reactions to the treatment. Thus, a human can be treated with an AMBP-1 (and adrenomedullin, when desired) from any mammalian species, but treatment with the human forms of these proteins is preferred. The AMBP-1 and adrenomedullin can also be from the same or different species. AMBP-1 and adrenomedullin from numerous species have been cloned and sequenced. Examples include the following GenBank accessions: Y00716 (human AMBP-1), NM 130409 (rat AMBP-1), NM 009888 (mouse AMBP-1), AAH15961 (human adrenomedullin), AAH61775 (rat adrenomedullin), AAH52665 (mouse adrenomedullin), NP 776313 (cow adrenomedullin), S41600 (pig adrenomedullin), and BAA96494 (horse adrenomedullin). Using this information, the skilled artisan could identify AMBP-1 and adrenomedullin from any other mammalian species without undue experimentation.

The AMBP-1 or adrenomedullin for these methods could also be a synthetic protein, not identical to that from any species. The skilled artisan could identify numerous such proteins, using the sequence information provided in the above-identified GenBank accessions, by simply altering one of the above sequences by, e.g., substituting amino acid residues (or nucleotides encoding the amino acids) from one species into the sequence of another species. Additionally, the AMBP-1 or adrenomedullin can be a peptidomimetic or other known forms that are more resistant to degradation than the natural polypeptides. Examples include groups such as amides or ester groups attached to the peptides, since such protected peptides would be deprotected in vivo to deliver the active adrenomedullin and AMBP-1.

Synthesis of the AMBP-1 or adrenomedullin for these methods can be by any known method, e.g., synthesis by peptide synthetic methods or, preferably, expression from an expression vector in bacterial, yeast, insect or mammalian cells.

These methods are useful for treatment of mammals undergoing, or at risk for, any type of ischemia-reperfusion injury, for example that to the bowel, the kidney, a lung, the myocardium, a crushed limb, the liver, a nerve, or to the brain, e.g., as a result of stroke or trauma. Ischemia-reperfusion injury to the kidney or liver is particularly common when the organ has been transplanted. Additionally, lung injury often accompanies ischemia-reperfusion in the intestine, particularly the bowel. The instant methods can reduce or eliminate this lung injury. See Example 2.

The amount of AMBP-1 administered will depend on the size and condition of the patient and can be determined without undue experimentation using standard dose-response protocols. Generally, the dosage of AMBP-1 of 0.2 to 200 µg/kg body weight, including, for example, 0.5, 1, 2, 5, 10, 25, 50 and 100 µg/kg, would be deemed appropriate, with the dosage on the low end of the dosage range being appropriate for the adult human. Where utilized, adrenomedullin of 0.1 to 100 µg/kg body weight, including, for example, 0.2, 0.5, 1, 2, 5, 10, 25 and 50 µg/kg is appropriate.

The above-described AMBP-1 and/or AM compositions can be formulated without undue experimentation for administration to a mammal, including humans, as appropriate for the particular application.

Accordingly, the compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The AMBP-1 and/or AM compositions of the present invention can easily be administered parenterally such as for example, by intravenous, intramuscular, intrathecal or subcutaneous injection. Parenteral administration can be accomplished by incorporating the compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the AMBP-1 and/or AM compositions into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

The present invention includes nasally administering to the mammal a therapeutically effective amount of the AMBP-1 and/or AM composition. As used herein, nasally administering or nasal administration includes administering the composition to the mucous membranes of the nasal passage or nasal cavity of the patient. As used herein, pharmaceutical compositions for nasal administration of a composition include therapeutically effective amounts of the composition prepared by well-known methods to be administered, for example, as a nasal spray, nasal drop, suspension, gel, ointment, cream or powder. Administration of the composition may also take place using a nasal tampon or nasal sponge.

The AMBP-1 (optionally with AM) can be administered prophylactically at any time before anticipated initiation of ischemia-reperfusion, for example before a transplant or angioplasty. Alternatively, the AMBP-1 can be administered during the ischemic or reperfusion event. Preferably, the AMBP-1 is administered within 90 minutes of the initiation of ischemia caused by the ischemia or subsequent reperfusion. When adrenomedullin is also administered, it can be administered before, during, or after administration of the AMBP-1.

The AMBP-1 (and adrenomedullin) can also be administered in conjunction with another agent that reduces a physiological effect of the ischemia-reperfusion. Nonlimiting examples of such agents include administration of pentoxifilline, allopurinol, or antibodies to neutrophil chemoattractants.

In other embodiments, the invention is directed to methods of treating a mammal at risk for ischemia-reperfusion injury to the bowel. The methods comprise administering adrenomedullin to the mammal in sufficient amount to reduce the injury.

As with the methods described above, the adrenomedullin can be from different, or preferably the same species as the mammal. These methods are also effective for any mammal, including humans. The adrenomedullin is preferably administered at 0.1-100 µg/kg body weight, as previously described, preferably by intravenous administration. Additionally, the adrenomedullin is preferably administered within 90 minutes of the ischemia, and before or at the same time as the reperfusion, although treatment after reperfusion can also be beneficial.

As discussed above, ischemia-reperfusion in the bowel can cause injury to the lungs. The instant embodiments can reduce the lung injury.

Preferred embodiments of the invention are described in the following Examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the Examples.

EXAMPLE 1

A Novel Approach to Downregulate Inflammatory Cytokines in Intestinal Ischemia-Reperfusion (I/R) Injury: The Role of Adrenomedullin (AM) and Adrenomedullin Binding Protein-1 (AMBP-1)

Objective: Ischemic bowel remains a critical clinical problem resulting in up to 80% mortality. This is in part related to reperfusion injury, which increases the release of inflammatory cytokines. Even though numerous modalities and substances have been studied to reduce I/R-induced mortality, none have been entirely successful. Since previous studies have shown that a novel vasodilatory peptide AM and its binding protein AMBP-1 have anti-inflammatory properties in a sepsis model, we hypothesize that administration of AM/AMBP-1 after intestinal I/R downregulates inflammatory cytokines and attenuates tissue injury.

Methods: Intestinal I/R was induced by superior mesenteric artery (SMA) clamping for 90 min and followed by reperfusion for 90 min in adult male rats. Upon release of the SMA clamp, treatment was given with either AM (12 µg/kg BW)/AMBP-1 (40 µg/kg BW) or vehicle (1-mL normal saline) via a femoral vein catheter over 30 min. At 60 min after the completion of the treatment, blood and tissue samples were collected and plasma levels of IL-1β, IL-6, IL-10 (pg/mL), lactate (mg/dL), creatinine (µmol/L) and liver enzymes (i.e., AST, IU/L) were measured. The animals with sham operation or ischemia 90 min only, did not receive AM/AMBP-1 treatment. Statistical analysis was performed using one-way ANOVA and Student-Newman-Keuls test.

Results: The data (mean±SE, n=7-8, *=p<0.05 vs. sham or ischemia 90'; #=p<0.05 vs. I/R+Vehicle) are shown in Table 1.

TABLE 1

|  | IL-1β | IL-6 | IL-10 | Lactate | Creatinine | AST |
| --- | --- | --- | --- | --- | --- | --- |
| Sham | 21 ± 4 | 78 ± 20 | 8 ± 4 | 14 ± 0.9 | 58 ± 8 | 54 ± 9 |
| Ischemia 90' | 26 ± 7 | 41 ± 9 | 9 ± 6 | 16 ± 1 | 63 ± 11 | 66 ± 7 |
| I/R + Vehicle | 81 ± 24* | 429 ± 118* | 159 ± 50* | 37 ± 4* | 120 ± 14* | 104 ± 12* |
| I/R + AM/AMBP-1 | 19 ± 4# | 134 ± 33# | 83 ± 18# | 29 ± 2*# | 79 ± 12# | 79 ± 3# |

The above results demonstrate that unlike ischemia 90 min alone, I/R significantly upregulated inflammatory cytokines IL-1β, IL-6 and IL-10. Moreover, I/R caused organ injury as evidenced by increased lactate, creatinine and AST levels. Administration of AM and AMBP-1 after ischemia, however, markedly reduced cytokine levels and attenuated tissue injury.

Conclusion: Since AM/AMBP-1 infusion dramatically downregulates inflammatory cytokines and protects organ function after intestinal I/R. AM/AMBP-1 appears to be a novel treatment to attenuate the reperfusion injury after an episode of ischemic bowel. These agents may reduce the morbidity and mortality associated with this disease entity.

EXAMPLE 2

Adrenomedullin (AM) and its Binding Protein (AMBP-1) Prevent Acute Lung Injury After Gut Ischemia/Reperfusion An ischemic bowel remains a critical problem resulting in up to 80% mortality. Acute lung injury induced by ischemia and reperfusion (I/R) injury may be responsible for such high mortality. Our previous studies have shown that administration of the vasoactive peptide AM, and its binding protein AMBP-1, reduces the systemic inflammatory response. However, it remains unknown whether AM/AMBP-1 has any protective effects on I/R-induced acute lung injury. To study this, intestinal I/R was induced by placing a microvascular clip across the superior mesenteric artery (SMA) for 90 min in adult male rats. Upon release of the SMA clamp, the animals were treated by either AM (12 μg/kg BW) in combination with AMBP-1 (40 μg/kg BW) or vehicle (1 ml normal saline) over a period of 30 min via a femoral vein catheter. The animals were euthanized 4 h later, and lung samples were assessed for granulocyte myeloperoxidase activity (MPO), water content, TNF-α, IL-6, IL-10 levels and morphological changes. Gene expression of the anti-inflammatory nuclear receptor, peroxisome proliferator-activated receptor-γ (PPAR-γ), was also measured. Results are as follows (mean±SEM; n=6-8/group):

TABLE 2

|  | Sham | I/R-Vehicle | I/R-AM/AMBP-1 |
|---|---|---|---|
| MPO (U/g protein) | 2.2 ± 0.1 | 6.4 ± 0.3* | 3.3 ± 0.2*# |
| Water content (%) | 75.0 ± 1.1 | 81.7 ± 0.7* | 75.8 ± 1.4# |
| TNF-α (ng/g protein) | 1.8 ± 0.1 | 3.1 ± 0.3* | 1.5 ± 0.4# |
| IL-6 (ng/g protein) | 52.3 ± 3.9 | 80.0 ± 9.6* | 53.6 ± 7.7# |
| IL-10 (ng/g protein) | 11.3 ± 1.2 | 19.3 ± 2.4* | 12.5 ± 2.7# |
| PPAR-γ/G3PDH (mRNA) | 0.30 ± 0.05 | 0.31 ± 0.04 | 0.44 ± 0.02*# |

(One-way ANOVA:
*$P < .05$ vs. Sham;
$P < .05$ vs. Vehicle)

Gene expression of the cytokines correlates with their protein levels (data not shown). Histological examination shows that AM/AMBP-1 restores the lung morphology to a level similar to that of the sham group. Our results demonstrate that administration of AM/AMBP-1 after intestinal ischemia prevents lung injury, downregulates inflammatory cytokines, and upregulates PPAR-γ expression. Thus, AM/AMBP-1 may be a novel treatment to attenuate acute lung injury after an episode of ischemic bowel. The beneficial effect of AM/AMBP-1 after I/R appears to be mediated by upregulation of PPAR-γ.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method of treating a mammal at risk for ischemia-reperfusion injury resulting from an ischemic bowel, the method comprising administering to the mammal an amount of adrenomedullin and adrenomedullin binding protein-1 (AMBP-1) effective to reduce ischemia-reperfusion injury in a mammal having an ischemic bowel.

2. The method of claim 1, wherein the mammal is a human.

3. The method of claim 1, wherein the AMBP-1 is administered at 0.2-200 μg/kg body weight.

4. The method of claim 1, wherein the adrenomedullin is administered at 0.1-100 μg/kg body weight.

5. The method of claim 1, wherein the AMBP-1 is administered within 90 minutes of the ischemia.

6. The method of claim 1, wherein the AMBP-1 is administered before or at the same time as the reperfusion.

7. The method of claim 1, wherein the AMBP-1 is administered after the reperfusion.

* * * * *